(12) United States Patent
Larnard et al.

(10) Patent No.: US 6,660,026 B2
(45) Date of Patent: Dec. 9, 2003

(54) MULTI-TIPPED COOLING PROBE

(75) Inventors: Donald J. Larnard, Hampton Falls, NH (US); Dan Sachs, Boston, MA (US)

(73) Assignee: Seacoast Technologies, Inc., Portsmouth, NH (US)

( * ) Notice: Subject to any disclaimer, the term of this patent is extended or adjusted under 35 U.S.C. 154(b) by 0 days.

(21) Appl. No.: 09/971,014

(22) Filed: Oct. 4, 2001

(65) Prior Publication Data

US 2002/0091425 A1 Jul. 11, 2002

Related U.S. Application Data

(60) Provisional application No. 60/238,314, filed on Oct. 5, 2000.

(51) Int. Cl.⁷ .................................................. A61F 7/12
(52) U.S. Cl. .......................... 607/104; 128/898; 607/96; 607/113
(58) Field of Search ................................ 607/105, 104, 607/110, 112, 113, 96; 128/898

(56) References Cited

U.S. PATENT DOCUMENTS

| | | | |
|---|---|---|---|
| 2,190,384 A | 2/1940 | Newman | 128/400 |
| 3,170,465 A | 2/1965 | Henney et al. | 128/401 |
| 3,174,481 A | 3/1965 | Seaman | 128/401 |
| 3,220,414 A | 11/1965 | Johnston | 128/400 |
| 3,504,674 A | 4/1970 | Swenson et al. | 128/303.1 |
| 3,736,936 A | 6/1973 | Basiulis et al. | 128/303.1 |
| 3,776,241 A | 12/1973 | Magilton et al. | 128/400 |
| 3,848,607 A | 11/1974 | St. Clair | 128/400 |
| 3,897,790 A | 8/1975 | Magilton et al. | 128/400 |
| 4,010,795 A | 3/1977 | Stenberg | |
| 4,207,897 A | 6/1980 | Lloyd et al. | 128/303.1 |
| 4,519,389 A * | 5/1985 | Gudkin et al. | 606/20 |
| 4,719,919 A | 1/1988 | Marchosky et al. | 128/401 |
| 4,781,193 A | 11/1988 | Pagden | 128/402 |
| 4,860,744 A | 8/1989 | Johnson et al. | 128/303.1 |
| 4,946,460 A | 8/1990 | Merry et al. | 606/24 |

(List continued on next page.)

FOREIGN PATENT DOCUMENTS

| | | |
|---|---|---|
| EP | B1 0132276 | 1/1985 |
| EP | B1 0382787 | 8/1990 |
| EP | B1 0586567 | 3/1994 |

(List continued on next page.)

OTHER PUBLICATIONS

Perov, et al., "Design of Thermodes for Cooling Sites of Cerebral Hemisphere Cortex in Chronic Tests", Sechenov Physiology Journal of the USSR, No. 7, 1983, Methods of Physiological Investigations, 5 pgs.

(List continued on next page.)

*Primary Examiner*—Linda C. M. Dvorak
*Assistant Examiner*—Henry M. Johnson
(74) *Attorney, Agent, or Firm*—Christopher & Weisberg, P.A.

(57) ABSTRACT

A method and device for thermally affecting tissue. The device having a thermal member and a contact probe in thermal communication with the thermal member. The device configured to provide a way to contact tissue with the contact probe and to thereby impart a thermal change to the tissue.

16 Claims, 2 Drawing Sheets

U.S. PATENT DOCUMENTS

| | | | |
|---|---|---|---|
| 4,989,601 A | 2/1991 | Marchosky et al. | 128/399 |
| 5,108,407 A | 4/1992 | Geremia et al. | |
| 5,207,674 A * | 5/1993 | Hamilton | 606/21 |
| 5,209,227 A * | 5/1993 | Deutsch | 607/104 |
| 5,261,399 A | 11/1993 | Klatz et al. | 607/104 |
| 5,304,214 A | 4/1994 | DeFord et al. | 607/105 |
| 5,334,181 A | 8/1994 | Rubinsky et al. | 606/22 |
| 5,380,319 A | 1/1995 | Saito et al. | 606/28 |
| 5,417,686 A | 5/1995 | Peterson et al. | 606/25 |
| 5,429,582 A | 7/1995 | Williams | 600/2 |
| 5,474,533 A | 12/1995 | Ward et al. | 604/26 |
| 5,520,682 A | 5/1996 | Baust et al. | 606/24 |
| 5,531,776 A | 7/1996 | Ward et al. | 607/105 |
| 5,540,711 A | 7/1996 | Kieturakis et al. | 606/192 |
| 5,549,559 A | 8/1996 | Eshel | 604/113 |
| 5,591,162 A | 1/1997 | Fletcher et al. | 606/25 |
| 5,607,443 A | 3/1997 | Kieturakis et al. | 606/192 |
| 5,609,620 A | 3/1997 | Daily | |
| 5,611,767 A | 3/1997 | Williams | 600/2 |
| 5,624,392 A | 4/1997 | Saab | 604/43 |
| 5,643,207 A | 7/1997 | Rise | 604/93 |
| 5,645,528 A | 7/1997 | Thome | 604/96 |
| 5,713,923 A | 2/1998 | Ward et al. | 607/3 |
| 5,716,353 A | 2/1998 | Matsuura et al. | 606/23 |
| 5,716,386 A | 2/1998 | Ward et al. | 607/106 |
| 5,718,584 A | 2/1998 | Wong | 433/168.1 |
| 5,718,684 A | 2/1998 | Gupta | 604/96 |
| 5,730,756 A | 3/1998 | Kieturakis et al. | 606/190 |
| 5,735,817 A | 4/1998 | Shantha | 604/100 |
| 5,772,680 A | 6/1998 | Kieturakis et al. | 606/190 |
| 5,814,014 A | 9/1998 | Elsberry et al. | 604/43 |
| 5,817,123 A | 10/1998 | Kieturakis et al. | 606/192 |
| 5,843,075 A | 12/1998 | Taylor | 606/34 |
| 5,871,498 A | 2/1999 | Jervis et al. | 606/192 |
| 5,891,134 A | 4/1999 | Goble et al. | |
| 5,899,898 A | 5/1999 | Arless et al. | 606/22 |
| 5,913,885 A | 6/1999 | Klatz et al. | 607/104 |
| 5,916,212 A | 6/1999 | Baust et al. | 606/22 |
| 5,916,242 A | 6/1999 | Schwartz | 607/113 |
| 5,928,203 A | 7/1999 | Davey et al. | 604/247 |
| 5,951,512 A | 9/1999 | Dalton | 604/93 |
| 5,954,714 A | 9/1999 | Saadat et al. | 606/28 |
| 5,957,963 A | 9/1999 | Dobak, III | 607/104 |
| 5,972,924 A | 10/1999 | Keep et al. | 514/183 |
| 5,976,109 A | 11/1999 | Heruth | 604/140 |
| 6,004,337 A | 12/1999 | Kieturakis et al. | 606/190 |
| 6,015,382 A | 1/2000 | Zwart et al. | 600/207 |
| 6,015,421 A | 1/2000 | Echeverry et al. | 606/190 |
| 6,017,324 A | 1/2000 | Tu et al. | 604/96 |
| 6,030,412 A | 2/2000 | Klatz et al. | 607/104 |
| 6,042,579 A | 3/2000 | Elsberry et al. | 604/891.1 |
| 6,045,532 A | 4/2000 | Eggers et al. | 604/114 |
| 6,051,019 A | 4/2000 | Dobak, III | 607/104 |
| 6,053,913 A | 4/2000 | Tu et al. | 606/41 |
| 6,073,051 A | 6/2000 | Sharkey et al. | 607/99 |
| 6,074,412 A | 6/2000 | Mikus et al. | 607/105 |
| 6,083,148 A | 7/2000 | Williams | 600/2 |
| 6,090,132 A | 7/2000 | Fox | 607/96 |
| 6,096,068 A | 8/2000 | Dobak, III et al. | 607/105 |
| 6,106,518 A | 8/2000 | Wittenberger et al. | 606/23 |
| 6,113,593 A | 9/2000 | Tu et al. | 606/34 |
| 6,117,128 A | 9/2000 | Gregory | 606/7 |
| 6,122,549 A | 9/2000 | Sharkey et al. | 607/99 |
| 6,123,718 A | 9/2000 | Tu et al. | 607/113 |
| 6,126,680 A | 10/2000 | Wass | 607/96 |
| 6,126,684 A | 10/2000 | Gobin et al. | 607/113 |
| 6,129,736 A | 10/2000 | Jervis et al. | 606/192 |
| 6,132,415 A | 10/2000 | Finch et al. | 604/502 |
| 6,146,411 A | 11/2000 | Noda et al. | 607/105 |
| 6,149,677 A | 11/2000 | Dobak, III | 607/106 |
| 6,152,920 A | 11/2000 | Thompson et al. | 606/41 |
| 6,156,057 A | 12/2000 | Fox | 607/96 |
| 6,168,608 B1 | 1/2001 | Echeverry et al. | 606/190 |
| 6,179,831 B1 | 1/2001 | Bliweis | 606/21 |
| 6,183,501 B1 | 2/2001 | Latham | 607/109 |
| 6,224,624 B1 | 5/2001 | Lasheras et al. | 607/105 |
| 6,238,428 B1 | 5/2001 | Werneth et al. | 607/105 |
| 6,248,126 B1 | 6/2001 | Lesser et al. | 607/113 |
| 6,251,129 B1 | 6/2001 | Dobak, III et al. | 607/105 |
| 6,251,130 B1 | 6/2001 | Dobak, III et al. | 607/105 |
| 6,322,559 B1 | 11/2001 | Daulton et al. | |
| 6,383,210 B1 * | 5/2002 | Magers et al. | 607/105 |

FOREIGN PATENT DOCUMENTS

| | | |
|---|---|---|
| RU | 211736 | 12/1966 |
| RU | 293381 | 12/1971 |
| RU | 432907 | 6/1974 |
| RU | 639557 | 12/1978 |
| RU | 833266 | 5/1981 |
| RU | A1 1138152 | 2/1985 |
| RU | A1 1544422 | 2/1990 |
| RU | A1 1745238 | 7/1992 |
| RU | A3 1787026 | 1/1993 |
| RU | C1 2100989 | 1/1998 |
| WO | WO 9603943 | 2/1996 |
| WO | WO 9934758 | 7/1999 |
| WO | WO 0007507 | 2/2000 |
| WO | WO 0059419 | 10/2000 |
| WO | WO 0117471 | 3/2001 |
| WO | WO 0176517 | 10/2001 |

OTHER PUBLICATIONS

Mursky, "On the Use of Complex (Cranial Cerebral and General) Hypothermia in Experiments", Brain Hypothermia, 1965, 4 pgs.

Shilo, et al., "Delivery/Dialysis Cannula for Local Superfusion of Brain Structures at Cranial Cerebral Hypothermia", Collection of Scientific Works, 1988, 3 pgs.

Rybakov, "Method of Intra–Ventricle Hypothermia of Brain", 3 pgs.

Fay, "Early Experiences with Local and Generalized Regrigeration of the Human Brain", Temple Fay, M.D., pp. 239–260.

Connolly, et al., "The protective of hypothermia in cerebal ischemia: Experimental and clinical application by selective brain cooling in the human", Dept. of Surgery, Stanford University School of Medicine, vol. 52, No. 1, Jul. 1962, pp. 15–24.

Kindt, et al., "Regional Hypothermia Produced by Cooling the Blood within the Intact Artery", Surgical Forum, 1966, 17: pp. 406–407.

Locke, et al., "Profound Selective Arterial Cooling of Brain without Pump or Oxygenator", Surgical Forum, 1965, 16: pp. 421–422.

Negrin, "An Instrument to Obtain Local Hypothermia of the Brain or Spinal Cord", International Surgery, Aug. 1970, vol. 54, No. 2, pp. 63–106.

* cited by examiner

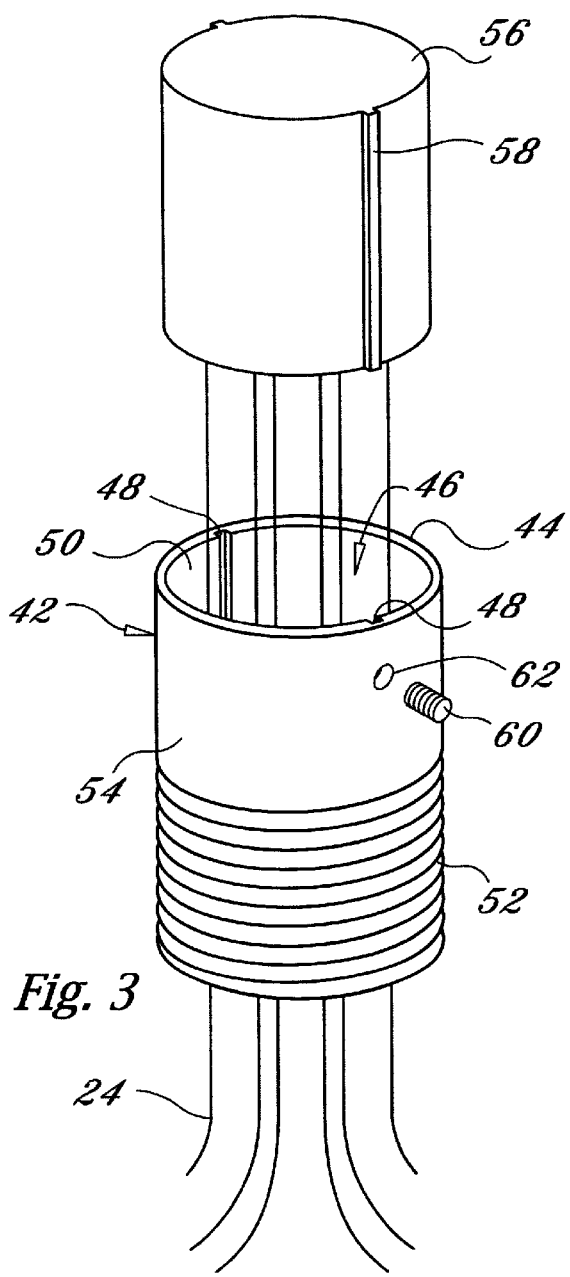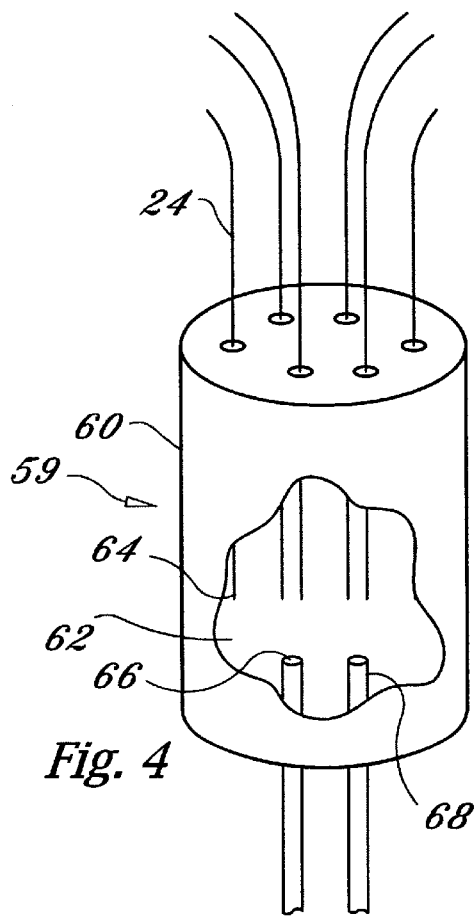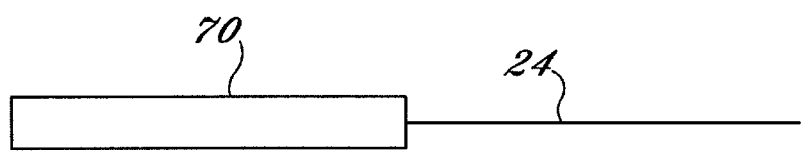
Fig. 3
Fig. 4
Fig. 5

US 6,660,026 B2

MULTI-TIPPED COOLING PROBE

CROSS-REFERENCE TO RELATED APPLICATION

This application is related to and claims priority to U.S. Provisional Patent Application Serial No. 60/238,314, filed Oct. 5, 2000, entitled SYSTEMS AND METHODS FOR CONTROLLING TEMPERATURE OF BRAIN TISSUE, the entirety of which is incorporated herein by reference.

STATEMENT REGARDING FEDERALLY SPONSORED RESEARCH OR DEVELOPMENT n/a

FIELD OF THE INVENTION

The present invention relates to systems and methods for controlling brain tissue temperature, and in particular to systems and methods for subcranial temperature control of brain tissue through the use of contact cooling devices.

BACKGROUND OF THE INVENTION

Many of the advantages of reducing or raising the temperature of a body tissue are well known. It has been found particularly desirable to lower the temperature of body in order to reduce the metabolism of the body. In stroke and several other pathological conditions, lowering the temperature of a body also reduces the permeability of the blood/brain barrier. Reduced body temperature also inhibits release of damaging neurotransmitters and inhibits calcium-mediated effects. Further, reduced body temperature has been found to inhibit brain edema and lower intracranial pressure. These and other advantageous effects of reduced body temperature are known in the art.

Prior art devices and methods affect a thermal change in a body by a systemic approach, meaning that the overall temperature of the entire body is lowered or raised to achieve the advantages noted above. Cooling the body has been particularly effective in surgical applications where reducing metabolism has made it possible to more easily accommodate lengthy operative procedures. An example of this systemic approach includes catheters for transferring heat to or from blood flowing within a patient's vessel. Closed loop heat exchange catheters are also known. Some of the disadvantages of systemic temperature reduction include the stimulation of cardiac arrhythmia, pulmonary edema and coagulopathies. Systemic temperature reduction also results in hypotension and various immunodeficiencies.

Further, a systemic approach is not always advantageous when the beneficial effects are desired locally at the focus of the operative procedure and only the disadvantages of temperature reduction are felt throughout the remainder of the body. As such, recent focus has been directed to producing temperature reduction in localized areas of the body, leaving the remainder of the body to function at a normal body temperature. Localized temperature reduction in known devices relies on the control of temperature through a wholly external device, for example using cooling helmets or cooling neck collars to produce localized temperature reduction for the brain. However, there are disadvantages associated with external cooling to affect internal tissue. For example, external methods do not allow a high enough resolution to allow selective tissue cooling. Some of the same disadvantages that are associated with thermally affecting the whole body can occur when using external cooling. When it is advantageous to apply thermal energy to a specified tissue location and not to other regions, the known external devices and their accompanying methods can not adequately accommodate these needs.

Therefore it is desirable to have a device and method for localized temperature control of a body part. Further, it is desirable to provide a way to apply thermal energy to a specific area of tissue, such as the brain, which is not ordinarily directly external to the body in a manner which minimizes trauma and the size of the body opening which must be created to access the tissue area.

SUMMARY OF THE INVENTION

The present invention overcomes the disadvantages of known systemic and external devices and techniques by providing localized brain cooling with a device placed through the skull.

The present invention provides a device and method for localized temperature control of a body part, such as the brain. In an exemplary embodiment, a device for thermally affecting tissue of a patient includes a housing defining an interior volume that is at least partially insertable into an exterior opening in a patient, such as a burr hole though the skull. A thermal member positioned within the interior volume of the housing includes a thermal input side and a thermal output side to impart a thermal change to a contact probe. The contact probe is in thermal communication with the thermal input side which in turn either facially contacts or penetrates the tissue and resultantly thermally affects the contacted tissue. An exemplary method of treatment using the device includes the steps of exposing tissue to be thermally affected; attaching a thermal device to an anchor point of the body; positioning the contact probe near, in or on the tissue; and operating the thermal member to thermally change the temperature of the tissue.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein:

FIG. 3 is an exploded view of another exemplary embodiment of a device constructed in accordance with the principles of the present invention;

FIG. 4 is a perspective view of still another exemplary embodiment of a device constructed in accordance with the principles of the present invention; and FIG. 5 is a perspective view of yet still another exemplary embodiment of a device constructed in accordance with the principles of the present invention.

DETAILED DESCRIPTION OF THE INVENTION

Figure 1:
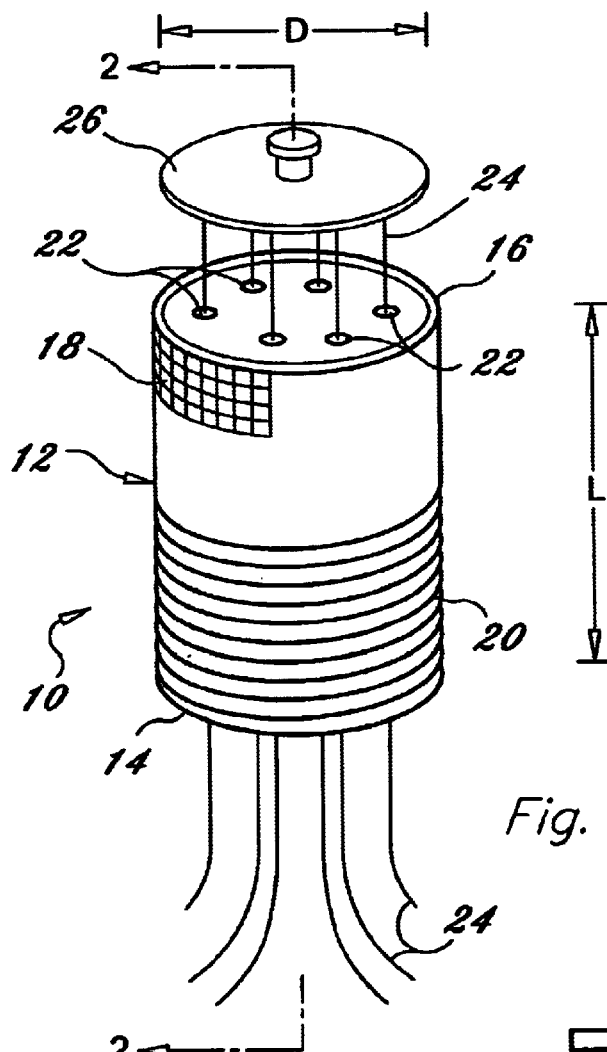
FIG. 1 is an exploded view of an exemplary embodiment of a device constructed in accordance with the principles of the present invention.

The present invention provides a device for applying thermal energy to a localized region of a body tissue. Referring now to the drawing figures in which like reference designators refer to like elements, there is shown FIG. 1 a perspective view of an exemplary embodiment of a device constructed in accordance with the principles of the present invention and designated generally as device 10. The device 10 includes a housing 12 with a first end 14, a second end 16 and an optional circulation vent 18 through which a thermally conductive fluid can pass. The housing 12 can be constructed of any suitable material, for example metals, plastics or a combination thereof. It is contemplated that the housing 12 has a diameter "D", measured at the widest portion of the device, from approximately one centimeter to approximately ten centimeters. In exemplary embodiments the diameter ranges from approximately 1 centimeters to 1.5 centimeters. Optional radial threads 20 are provided on the exterior of the housing 12 to facilitate attachment to bone structure such as a skull. However, it is contemplated that non-threaded arrangements can also be provided or coupled to or on the housing 12, for example, flutes, barbs, ridges or other anchoring elements. The device 10 has one or more conduits 22 which run through the housing 12. The conduits 22 are configured to accept one or more respective contact probes 24, which are slidable within the conduits 22 along a direction L. Further, an advancement member 26 is provided to facilitate sliding of the contact probes 24. The contact probes 24 are configured to contact a tissue to be treated or to be inserted into tissue to be treated. During operation, the contact probes 24 have a reduced temperature relative to a tissue to be treated. Alternatively, the contact probes 24 can be constructed to have a reduced temperature along their entire length, or a lesser portion thereof, for example only at a distal end. The contact probes can be constructed from any resilient, thermally conductive material, for example, NiTi alloy, stainless steel, titanium, steel, or aluminum.

Figure 2:
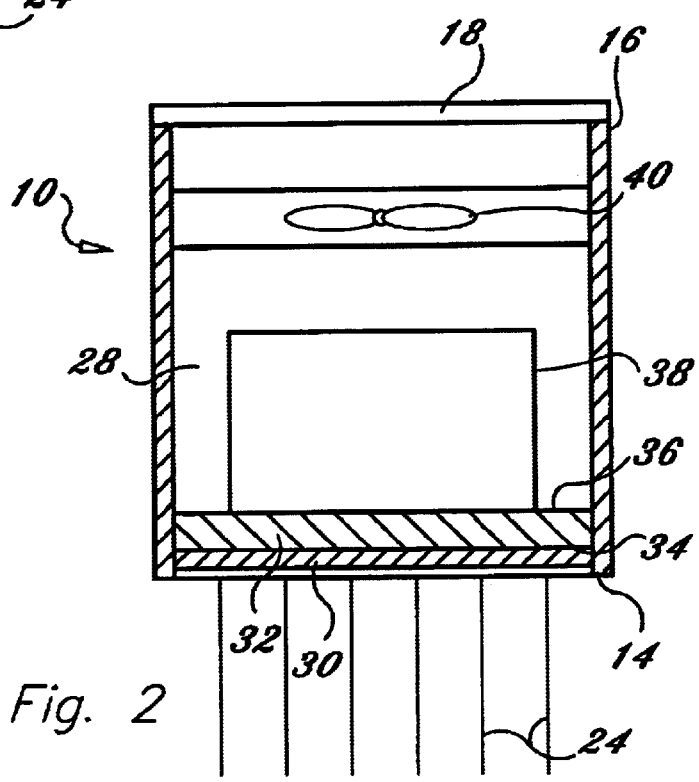
FIG. 2 is a section view taken along section 2—2 of FIG. 1.

FIG. 2 is a section view taken along section 2—2 of FIG. 1. FIG. 2 shows an embodiment where the contact probes 24 are fixed or embedded within a conduction member 30. In a configuration as is shown in FIG. 1, the conduits 22 would be in communication with the conduction member 30 which would in turn have passageways for the contact probes 24. However, when the contact probes 24 are fixed, conduits 22 through the housing 12 are not necessary and the contact probes 24 can be embedded in the conduction member 30 as shown in FIG. 2. The housing 12 is arranged as a circumferential wall which defines an interior space 28. Provided within the interior space 28, starting at the first end 14 and moving toward the second end 16, is the conduction member 30 which is configured to be in thermal communication with the contact probes 24. The conduction member 30 can be constructed of any thermally conductive material, for example, stainless steel, aluminum, copper, titanium, various polymers or other such materials. Additionally, adjacent the conduction member 30 is a thermal member 32. The thermal member 32 has a thermal input side 34 in thermal communication with the conduction member 30 and a thermal output side 36. The thermal member 32 can be a thermoelectric cooler, for example, a peltier cooler. Optionally, a thermal dissipation member 38 is provided in thermal communication with the output side 36 of the thermal member 32. Such devices are known in the art, for example, a common thermal dissipation member is a heat sink. However, many alternate components for dissipating thermal energy can be provided.

Further provided within the housing 12 in the interior space 28 is a fluid circulation member 40. The term "fluid" as used herein generally refers to any flowable substance, including but not limited to gasses and liquids. An exemplary fluid circulation member 40 is a cooling fan. The fluid circulation member 40 is positioned such that it circulates a fluid, such as air, across the thermal output side 36 of the thermal member 32 or the optional thermal dissipation member 38 if provided, thereby removing thermal energy dissipated by the thermal member 32. Alternatively, it is contemplated that a pump used in association with a thermally conductive liquid can be provided to dissipate thermal energy generated by the output side 36 of the thermal member 32.

Referring to FIG. 2, the operation of an exemplary device is now discussed in detail. Power is supplied to the thermal member 32 through electrical wires (not shown) which in turn creates a thermal input side 34 and a thermal output side 36 to the thermal member 32 (the thermal member discussed here is a peltier effect cooler and its function is well known in the art). By operation of the thermal member 32, the thermal input side 34 has a reduced temperature relative to the thermal output side 36 which causes a cooling effect at the thermal input side 34. The thermal input side 34 being in thermally conductive contact with the conduction member 30, thereby causes a reduction of the relative temperature of the conduction member 30, which in turn causes a reduced temperature in the contact probes 24. The thermal output side 36 being in thermally conductive contact with the optional thermal dissipation member 38 thereby raises the relative temperature of the thermal dissipation member 38 (creating heat). Additionally, power or activation energy is supplied to the fluid distribution member 40 to thereby circulate air through the thermal dissipation member 38 and out of housing 12 through the circulation vent 18. Heat dissipated by the thermal dissipation member 38 is removed and discharged from the housing 12 to maintain a reduced temperature at the conduction member 30. The contact probes 24 are configurable to contact tissue and thereby impart a thermal change on the tissue. As such, the concepts of the present invention provide a device 10 for localized cooling of a tissue in a compact package.

FIG. 3 is an exploded view of an alternate arrangement of the structure of a device in accordance with the principles of the present invention. FIG. 3 shows an insert housing 42 having an insert wall 44 which defines an inner volume 46. Longitudinal grooves 48 are provided on an inner surface 50 of the insert wall 44. Radial threads 52 for fastening the insert housing 42 to the bone structure of a skull are provided on an outer surface 54 of the insert wall 44. Further, FIG. 3 shows a thermal cartridge 56 having a size provided to substantially fit within the inner volume 46 of the insert housing 42. Thermal cartridge 56 has axial slots 58 configured to be slidably engagable with axial grooves 48 of the insert housing 42. The thermal cartridge 56 includes the exemplary elements as discussed above for applying thermal energy to a tissue site, for example, contact probes, a conduction member, a thermal member, and a cooling fan (not shown). In practice, the insert housing 42 is fixedly attached within a skull opening, for example by screwing the radial threads into the bone structure of a skull. The thermal cartridge 56 is then inserted into the inner volume 46 of the insert housing 42 while aligning the axial slots 58 with the axial grooves 48. The thermal cartridge 56 can be slidably adjusted within the insert housing 42 in order to specifically locate the contact probes 24 adjacent a tissue treatment site.

Once a desired distance of insertion is reached, the thermal cartridge 56 is held in position by a stop fastener 60 through a stop fastener opening 62 in the insert housing 42. While FIG. 3 illustrates an axial groove and slot arrangement, it is contemplated that alternate configurations can be provided. For example, a spiral groove and slot arrangement can be provided which would provide insertion depth adjustment via rotation of the thermal cartridge relative to the insertion housing. Further, it is contemplated that the locations of the groove and slot can be reversed, and further that alternate structures can be employed to effect the same result.

FIG. 4 is a perspective view of still another device constructed in accordance with the principles of the invention. FIG. 4 shows a device 59 which is configured to be inserted into an opening in a patient. The device 59 has a housing 60, which is shown in partial cut-away. The housing 60 defines an interior volume 62. Provided within the interior volume 62 is an end 64 of the contact probe 24. Also provided within the interior volume 62 is a coolant inlet 66 and a coolant outlet 68. In use, a coolant is circulated through the coolant inlet 66 into the interior volume 62 where the coolant imparts a thermal change to the end 64 of the contact probe 24, and the contact probe 24 is thereby thermally affected. The coolant is then circulated out of the interior volume 62 via the coolant outlet 68. By this operation thermal energy is imparted to the contact probes 24, which thereby affect a tissue to be treated. It will be readily understood that different types of coolants can be utilized, for example, chilled water, saline, nitrous oxide, nitrogen or any other such suitable thermally transmissive fluid.

FIG. 5 is a perspective view of yet still another device constructed in accordance with the present invention. FIG. 5 shows a single contact probe 24 and a handle 70. The handle is configured to allow a user to manipulate the contact probe 24 to a desired treatment location within a patient. Further provided within the handle is a device for thermally affecting the contact probe 24, as described herein.

In view of the preceding disclosure, the present invention provides a device which is used to impart a thermal change on a tissue medium. The present invention advantageously provides a user with an ability to control the temperature of a localized region of brain tissue. A procedure using the device of the present invention is accomplished by inserting the contact probe 24 into a burr hole in the skull. An exemplary application is to directly contact brain tissue with the contact probe 24 in order to lower the localized brain temperature as a neuroprotective measure in a post-stroke condition. The device provides the contact probe 24 which is used to penetrate brain tissue and cause local cooling of brain tissue. Alternatively, this device could also be used to cool localized regions of the brain in a brain trauma patient as a means of lowering cerebral metabolic requirements and minimizing brain edema. Furthermore, this device could also be used in any post-operative trauma situation when the possibility of cerebral edema exists and it is desired to be abated or minimized. Alternatively, the contact probe 24 could be placed into lateral ventricle(s) of brain to cool CSF (cerebral spinal fluid) which will circulate throughout the brain. It is contemplated that thermal therapy could involve either chilled or heated portions of the device to achieve desired result. The contact probe 24 being used to penetrate brain tissue to the center of an infarct or to the perimeter of an infarct is also contemplated. Such a device is used to cool deep tissues and to access areas/infarct regions deep in the brain that cannot necessarily be reached using surface cooling methods.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A device for thermally affecting tissue of a patient, comprising:
   a housing, the housing defining an interior volume and being at least partially insertable into an exterior opening in the patient;
   a thermal member having a thermal input side and a thermal output side, at least a portion of the thermal member being positioned within the interior volume, one of the thermal input side and the thermal output side being arrangable to provide a temperature different than the other of the thermal input side and the thermal output side; and
   a plurality of contact probes in thermal communication with the thermal input side configured to impart a thermal change to the tissue.

2. The device according to claim 1, wherein the thermal member is a peltier effect cooler.

3. The device according to claim 1, wherein the contact probe is manufactured of resilient, thermally conductive material.

4. The device according to claim 3, wherein the resilient, thermally conductive material is selected from the group consisting of titanium, stainless steel, aluminum, steel, and NiTi thereof.

5. A device for thermally affecting tissue of a patient, comprising:
   a housing, the housing defining an interior volume;
   a thermal fluid input, the thermal fluid input being in fluid communication with the interior volume and configured to introduce a thermal fluid into the interior volume;
   a thermal fluid output, the thermal fluid output being in fluid communication with the interior volume and configured to remove the thermal fluid from the interior volume; and
   a probe, the probe being configured to be in direct thermal communication with the introduced thermal fluid.

6. A method of treatment of brain tissue comprising the steps of:
   creating an opening in a skull;
   inserting a plurality of contact probes into the skull and contacting the brain tissue to be treated; and
   affecting a temperature change of the contact probe and thereby affecting a temperature change of the brain tissue.

7. A method of thermally affecting brain tissue of a patient, comprising:
   inserting a contact probe into a brain cavity,
   disposing the contact probe proximate to one or more cerebrospinal fluid spaces of the brain of said patient; and
   affecting a temperature charge of the contact probe and thereby thermally affecting cerebrospinal fluid in the one or more cerebrospinal fluid spaces to induce a temperature change of said brain tissue.

8. The method of claim 7, wherein the one or more cerebrospinal fluid spaces is a lateral ventricle.

9. The method of claim 7,
   wherein the contact probe is coupled to a thermal transfer device comprising:
      a housing, the housing defining an interior volume;
      a thermal fluid input, the thermal fluid input being in fluid communication with the interior volume and configured to introduce a thermal fluid into the interior volume;

a thermal fluid output, the thermal fluid output being in fluid communication with the interior volume and configured to remove the thermal fluid from the interior volume; and wherein the contact probe is configured to be thermally affected by the thermal fluid in the interior.

10. The method of claim 7, wherein the contact probe is coupled to a thermal transfer device comprising:
   a housing, the housing defining an interior volume and being at least partially insertable into an exterior opening in the patient;
   a thermal member having a thermal input side and a thermal output side, at least a portion of the thermal member being positioned within the interior volume, one of the thermal input side and the thermal output side being arrangable to provide a temperature different than the other of the thermal input side and the thermal output side; and
wherein the contact probe is in thermal communication with the thermal input side configured to impart a thermal change to the tissue.

11. The method of claim 10, wherein the thermal member is a peltier effect cooler.

12. The method of claim 7, further comprising: creating an opening in a skull of the patient to access the brain cavity.

13. A method of selectively cooling a first brain tissue region in a patient, comprising:

inserting a contact probe into the brain proximate the first brain tissue region, disposing the contact probe to contact cerebral spinal fluid in one or more cerebrospinal fluid spaces, cooling the cerebral spinal fluid in the one or more cerebrospinal fluid spaces to induce cooling of the first brain tissue region.

14. The method of claim 13, wherein the one or more cerebrospinal fluid spaces includes one of a lateral ventricle of the brain.

15. The method of claim 13, wherein the contact probe is coupled to a thermal transfer device comprising:
   a housing, the housing defining an interior volume;
   a thermal fluid input, the thermal fluid input being in fluid communication with the interior volume and configured to introduce a thermal fluid into the interior volume;
   a thermal fluid output, the thermal fluid output being in fluid communication with the interior volume and configured to remove the thermal fluid from the interior volume; and
wherein the contact probe is configured to be thermally affected by the thermal fluid in the interior.

16. The method of claim 13, further comprising:

creating one or more openings in a skull of the patient, and inserting the contact probe through the one or more openings.

* * * * *

UNITED STATES PATENT AND TRADEMARK OFFICE
CERTIFICATE OF CORRECTION

PATENT NO. : 6,660,026 B2
DATED : December 9, 2003
INVENTOR(S) : Donald J. Larnard et al.

It is certified that error appears in the above-identified patent and that said Letters Patent is hereby corrected as shown below:

Column 6,
Line 25, change from "thereof" to -- alloy --.
Line 54, change from "charge" to -- change --.

Column 8,
Line 3, change from "cerebral spinal" to -- cerebrospinal --.

Signed and Sealed this

Twenty-seventh Day of September, 2005

JON W. DUDAS
*Director of the United States Patent and Trademark Office*